(12) United States Patent
Hu et al.

(10) Patent No.: US 8,518,891 B2
(45) Date of Patent: Aug. 27, 2013

(54) CHEMOTHERAPEUTIC CONJUGATES AND METHODS OF USE

(76) Inventors: Longqin Hu, Piscataway, NJ (US); Xinghua Wu, Piscataway, NJ (US)

( * ) Notice: Subject to any disclaimer, the term of this patent is extended or adjusted under 35 U.S.C. 154(b) by 496 days.

(21) Appl. No.: 12/516,815

(22) PCT Filed: Nov. 29, 2007

(86) PCT No.: PCT/US2007/085981
§ 371 (c)(1),
(2), (4) Date: May 29, 2009

(87) PCT Pub. No.: WO2008/067495
PCT Pub. Date: Jun. 5, 2008

(65) Prior Publication Data
US 2010/0075927 A1 Mar. 25, 2010

Related U.S. Application Data

(60) Provisional application No. 60/861,548, filed on Nov. 29, 2006.

(51) Int. Cl.
*A61K 38/00* (2006.01)
*A61K 31/435* (2006.01)
(52) U.S. Cl.
USPC .......................... 514/19.5; 514/19.2; 514/277

(58) Field of Classification Search
None
See application file for complete search history.

(56) References Cited

U.S. PATENT DOCUMENTS

| | | | | |
|---|---|---|---|---|
| 5,659,061 A | * | 8/1997 | Glazier | ......................... 558/166 |
| 5,948,750 A | | 9/1999 | Garsky et al. | |
| 2003/0096743 A1 | * | 5/2003 | Senter et al. | .................... 514/12 |

FOREIGN PATENT DOCUMENTS

| | | | |
|---|---|---|---|
| WO | WO 98/18493 | * | 5/1998 |
| WO | WO 98/52966 | * | 11/1998 |

\* cited by examiner

*Primary Examiner* — Christina Bradley
(74) *Attorney, Agent, or Firm* — Fox Rothschild LLP

(57) ABSTRACT

Chemotherapeutic conjugates of a peptide substrate to a phosphoramide chemotherapeutic agent in which a peptide substrate is covalently linked to the chemotherapeutic agent by a linker with an aminoarylmethyl or aminoheteroaryl moiety, wherein the linking of the peptide to the chemotherapeutic agent inhibits the cytotoxic activity of the chemotherapeutic agent, the peptide is a substrate for proteolytic cleavage by a tumor-specific enzyme; and the linker is capable of undergoing 1,6-elimination in vivo upon cleavage of the peptide substrate. Methods for synthesizing and methods of using the conjugates are also disclosed.

5 Claims, 3 Drawing Sheets

| Entry | Azide |
|---|---|
| 1 | $O_2N$–C$_6$H$_4$–$N_3$ |
| 2 | $NC$–C$_6$H$_4$–$N_3$ |
| 3 | $HOOC$–C$_6$H$_4$–$N_3$ |
| 4 | (PhO)$_2$P(O)–$N_3$ |
| 5 | 4-MeC$_6$H$_4$–$SO_2N_3$ |
| 6 | PhC(O)–$N_3$ |
| 7 | 2,3,4,6-tetra-O-acetyl-β-D-glucopyranosyl azide |
| 8 | $MeO$–C$_6$H$_4$–$N_3$ |
| 9 | $HOCH_2$–C$_6$H$_4$–$N_3$ |
| 10 | $AcOCH_2$–C$_6$H$_4$–$N_3$ |
| 11 | $H_2N$–C$_6$H$_4$–$N_3$ |
| 12 | $TBDPSO$–$(CH_2)_6$–$N_3$ |

Fig. 3.

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Hydroxyproline
<220> FEATURE:
<221> NAME/KEY: misc_feature
<222> LOCATION: (4)..(4)
<223> OTHER INFORMATION: Cyclohexylglycine

<400> SEQUENCE: 1

Pro Ala Ser Xaa Gln
1               5

<210> SEQ ID NO 2
<211> LENGTH: 6
<212> TYPE: PRT
<213> ORGANISM: Artificial
<220> FEATURE:
<223> OTHER INFORMATION: Synthetic Peptide Substrate

<400> SEQUENCE: 2

His Ser Ser Lys Leu Gln
1               5

<210> SEQ ID NO 3
<211> LENGTH: 4
<212> TYPE: PRT
<213> ORGANISM: Artificial
<220> FEATURE:
<223> OTHER INFORMATION: Synthetic Peptide Substrate

<400> SEQUENCE: 3

Ser Ser Phe Tyr
1
```

CHEMOTHERAPEUTIC CONJUGATES AND METHODS OF USE

RELATED APPLICATIONS

This application is a National Stage filing under 35 U.S.C. §371(c) of International Application Serial No. PCT/US07/085981 filed Nov. 29, 2007. PCT/US07/085971 claims priority to a U.S. Provisional Application No. 60/861,547 filed on Nov. 29, 2006, both of which are incorporated herein by reference.

FIELD OF INVENTION

The invention relates to target-selective chemotherapeutic conjugates of a peptide substrate to a chemotherapeutic agent, and more particularly to peptide substrates covalently linked to cytotoxic chemotherapeutic agents by linkers comprising an aminoarylmethyl moiety.

BACKGROUND

Cyclophosphamide is an anticancer drug used in the treatment of a variety of cancers. It is administered in inactive form and is activated in the liver cytochrome P-450 pathway. After activation, the cytotoxic metabolites include phosphoramide mustard. Phosphoramide mustard forms DNA cross-links between (interstrand crosslinkages) and within (intra-strand crosslinkages) DNA strands at guanine N-7 positions. This leads to cell death. While the cytotoxic metabolites produce the desired anticancer effect in tumor tissues, it is also distributed to normal tissues where it causes adverse effects.

Peptide conjugates are formed by attaching a chemotherapeutic agent to a peptide either directly or through a linker. They are designed so the chemotherapeutic agent is inactive until the conjugate is cleaved by a tumor-specific enzyme in close proximity to tumor tissues. This increases the selectivity of the chemotherapeutic agent in killing cancer cells while decreasing adverse effects elsewhere in the system.

The peptides may be attached to the chemotherapeutic drugs either directly or through a linker. U.S. Pat. No. 7,091,186, for example, discloses self-immolative linkers that allow the release of fully active, chemically unmodified drug from the peptide. However, the methods of using such linkers disclosed in the '186 patent are not suitable for use with phosphoramide chemotherapeutic drugs. Accordingly, there is still a need in the art for methods of synthesis of phosphoramide chemotherapeutic conjugates.

SUMMARY

In one aspect, target-selective chemotherapeutic conjugates of a peptide substrate to a phosphoramide chemotherapeutic agent are provided in which a peptide substrate is covalently linked to the phosphoramide group of the chemotherapeutic agent by a linker containing an aminoarylmethyl or an aminoheteroaryl moiety, wherein the linking of the peptide substrate to the chemotherapeutic agent inhibits the cytotoxic activity of the chemotherapeutic agent, the peptide substrate is subject to proteolytic cleavage by an enzyme specific to a tumor responsive to treatment by the chemotherapeutic agent; and the linker is susceptible to 1,6-elimination in vivo.

In one embodiment, the tumor-specific enzyme is a prostate specific antigen (PSA), and the peptide substrate contains at least 3 amino acids, one of which is a GLN, such as Hyp-Ala-Ser-Chg-Gln, attached to the amino-end of said linker.

Specific examples of phosphoramide chemotherapeutic agents include phosphoramide mustards of the following formula:

(1)

wherein at least one of $R_3$, $R_4$, $R_5$ and $R_6$ is $CH_2CH_2Y$ and Y is a halogen, preferably Cl or Br, and any remaining $R_3$, $R_4$, $R_5$ or $R_6$ groups may each independently be a hydrogen or a lower alkyl group.

In one embodiment, a target-selective chemotherapeutic conjugate is of formula 2:

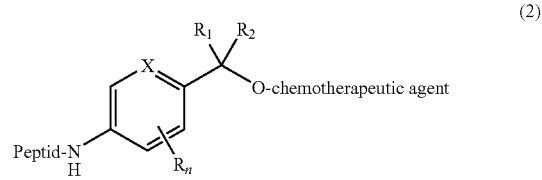

(2)

in which: X is CH or N; R is selected from H or an electron-withdrawing group, examples of which include F, Cl, $CF_3$, CN, $NO_2$, and the like; n is 0, 1, 2, 3 or 4; $R_1$ and $R_2$ may each independently be a hydrogen, lower alkyl, alkoxyalkyl, carboxylalkyl, or amidoalkyl group; the chemotherapeutic agent is a phosphoramide mustard according to Formula (1); and the peptide is a peptide substrate subject to cleavage by a tumor-specific enzyme. $R_n$ may be selected from 2-F, 3-F, 2,6-di-F or 2,3,5,6-tetra-F when X is CH and 3-F, 4-F, 6-F, 3,6-di-F or 3,4,6-tri-F when X is N.

In another embodiment, the target-selective chemotherapeutic conjugate is of formula 3:

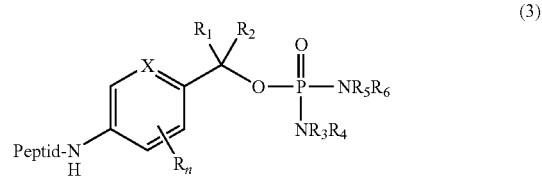

(3)

in which X is CH or N; R is selected from H or an electron-withdrawing group, examples of which include F, Cl, $CF_3$, CN, $NO_2$, and the like; n is 0, 1, 2, 3, or 4; $R_1$ and $R_2$ may each independently be a hydrogen, lower alkyl, alkoxyalkyl, carboxylalkyl, or amidoalkyl group; at least one of $R_3$, $R_4$, $R_5$ and $R_6$ is $CH_2CH_2Y$ and Y is a halogen, preferably Cl or Br, and any remaining $R_3$, $R_4$, $R_5$ or $R_6$ groups may each independently be a hydrogen or a lower alkyl group; and the peptide is a peptide substrate subject to cleavage by a tumor-specific enzyme. Preferably, $R_n$ is selected from 2-F, 3-F, 2,6-di-F, or 2,3,5,6-tetra-F when X is CH and 3-F, 4-F, 6-F, 3,6-di-F or 3,4,6-tri-F when X is N.

In another embodiment an intermediate compound for the preparation of the conjugate of Formula 1 is provided having the structure of Formula 4:

(4)

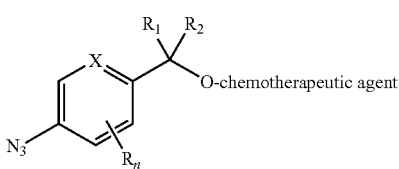

in which X is CH or N; R is selected from H or an electron-withdrawing group, examples of which include F, Cl, $CF_3$, CN, $NO_2$; is 0, 1, 2, 3 or 4; $R_1$ and $R_2$ may each independently be a hydrogen, lower alkyl, alkoxyalkyl, carboxylalkyl, or amidoalkyl group; and the chemotherapeutic agent is selected from phosphoramide mustard, taxol, doxorubicin, vinblastine, thapsigargen, and their analogs with amino, hydroxyl, and carboxylic acid groups, and the like, covalently bonded to the linker.

In another embodiment an intermediate compound for the preparation of the conjugate of Formula 2 is provided, having the structure of Formula 5:

(Amine protecting group)-Gln-Se$^-$M$^+$      (5)

in which preferred protecting groups are selected from $CF_3CO$, Cbz, Fmoc, and Boc and M is a counterion such as H or a metal or an organic base.

In another embodiment an intermediate compound for the preparation of the conjugate of Formula 2 is provided, prepared from the intermediate compounds of Formula 4 and of Formula 5, and having the structure of Formula 6:

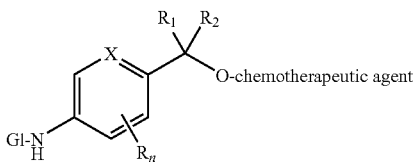

(6)

in which X is CH or N; R is selected from H or an electron-withdrawing group, examples of which include F, Cl, $CF_3$, CN, $NO_2$; n is 0, 1, 2, 3 or 4; $R_1$ and $R_2$ may each independently be a hydrogen, lower alkyl, alkoxyalkyl, carboxylalkyl, or amidoalkyl group; and the chemotherapeutic agent is selected from phosphoramide mustard, taxol, doxorubicin, vinblastine, thapsigargen, and their analogs with amino, hydroxyl, and carboxylic acid groups, and the like, covalently bonded to the linker.

Another aspect provides methods for coupling a carboxylic acid and an azide by activating a carboxylic acid with a chloroformate, such as isopropyl chloroformate, in the presence of N-methylpiperidine or in situ with HBTU, TBTU, HATU, BOP, PyBOP, or PyAOP; reacting the compound formed in the previous step with LiAlHSeH or NaHSe to form a selenocarboxylate; and reacting the selenocarboxylate with an azide to form an amide. Azides suitable for these methods include 4-azidobenzyl and 5-azidopyridinyl-2-methyl compounds having the structure: $N_3$-Ph-$CR_1R_2$-$R_7$, wherein $R_1$ and $R_2$ may each independently be a hydrogen, lower alkyl, alkoxyalkyl, carboxylalkyl, or amidoalkyl group; Ph is substituted or unsubstituted phenyl or pyridinyl; and $R_7$ is selected from hydroxyl, ester, carbamate, phosphate and phosphoramidate.

In yet another aspect, methods for synthesizing a target-selective chemotherapeutic conjugate of a peptide substrate and a chemotherapeutic agent are provided. These methods include synthesizing an azide compound by a reaction that covalently bonds an azidoaryl or azidopyridinyl compound to a phosphate, phosphoramide, amino or carboxylic acid group of a chemotherapeutic agent; reacting an N-protected amino acid selenocarboxylate and the azide compound to convert the azidoaryl covalently bonded to the chemotherapeutic agent to an N-protected-amino acid-amidoaryl; and reacting the amino acid-amidoaryl group covalently bonded to the chemotherapeutic agent with a carboxy-activated peptide substrate to conjugate the substrate to the chemotherapeutic agent. The peptide substrate is subject to proteolytic cleavage by an enzyme specific to a tumor responsive to treatment by the chemotherapeutic agent.

Another aspect provides methods for treating cancer in a patient by administering to the patient a composition containing the target-selective chemotherapeutic conjugate as described above, wherein the peptide of the conjugate is a substrate for proteolytic cleavage by an enzyme specific to the cancer.

In yet another aspect, target-selective chemotherapeutic conjugates of a peptide substrate to a chemotherapeutic agent are provided in which a peptide substrate is covalently linked to the chemotherapeutic agent by a linker having the following structure:

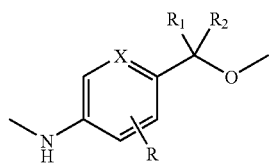

(7)

in which X is CH or N; $R_1$ and $R_2$ may each independently be a hydrogen, lower alkyl, alkoxyalkyl, carboxylalkyl, or amidoalkyl group; the peptide is a peptide substrate subject to cleavage by a tumor-specific enzyme; and $R_n$ may be selected from 2-F, 3-F, 2,6-di-F or 2,3,5,6-tetra-F when X is CH and 3-F, 4-F, 3,6-di-F or 3,4,6-tri-F when X is N; wherein the linking of the peptide substrate to the chemotherapeutic agent inhibits the cytotoxic activity of the chemotherapeutic agent, the peptide substrate is subject to proteolytic cleavage by an enzyme specific to a tumor responsive to treatment by the chemotherapeutic agent; and the linker is susceptible to 1,6-elimination in vivo.

BRIEF DESCRIPTION OF THE FIGURES

FIG. 3 presents examples of azides suitable for use in methods described herein.

DETAILED DESCRIPTION

Figure 1:
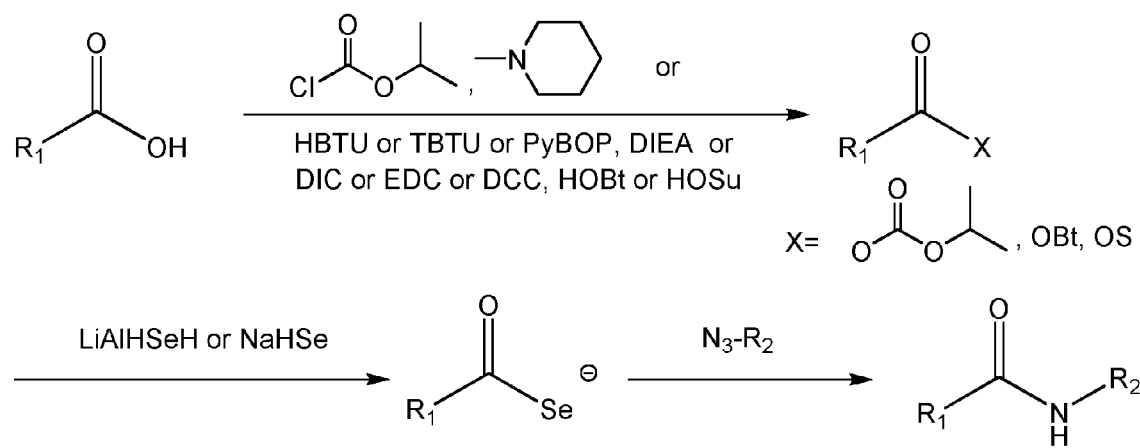
FIG. 1 presents a scheme of the synthesis of amides from azides and carboxylic acids.

In one aspect, target-selective chemotherapeutic conjugates of a peptide substrate to a chemotherapeutic agent are provided that heretofore were not possible to make.

The peptide substrate is selected to provide a substrate for proteolytic cleavage by enzymes specific to tumors responsive to treatment by phosphoramides. Such conjugates have a peptide substrate covalently linked to the cytotoxic agent by an amino-aryl-methyl or amino-heteroaryl-methyl moiety-containing linker where the linking of the peptide to the chemotherapeutic agent inhibits the cytotoxic activity of the chemotherapeutic agent. The linker becomes susceptible to 1,6-elimination in vivo upon cleavage of the peptide to restore the cytotoxic activity of the chemotherapeutic agent. The linker may also include substituents by electron-withdrawing groups such as fluorine, cyano, and nitro in order to increase the conjugate's stability.

Peptide Substrates:

Peptides provide substrates for proteolytic cleavage by enzymes. The terms "peptide" and "protein" are used interchangeably herein to refer to a polymer with at least one naturally occurring or synthetic amino acid residue. The term encompasses amino acid chains of any length and also includes compounds that include moieties other than amino acids. The term "peptide substrate" specifically refers to a peptide that includes a cleavage site for a tumor-specific enzyme.

Suitable peptide substrates are subject to proteolytic cleavage by enzymes specific to tumors responsive to treatment by the chemotherapeutic agent linked to that peptide substrate. On the other hand, the peptide substrates are preferably stable toward cleavage by other enzymes in the body to eliminate, or at least minimize, the systemic toxicity of the chemotherapeutic agent. Examples of tumor-specific enzymes capable of proteolytically cleaving the peptide substrates include but are not limited to prostate specific antigen (PSA), carboxypeptidase, plasmin, matrix metalloproteinase and Cathepsin E.

The peptides and peptide substrates may be synthesized by any known technique used in the art. For example, they may be synthesized by standard solid peptide synthesis (Barany, G. and Merrifield, R. B., The Peptides 2:1 284, Gross, E. and Meienhofer, J., Eds., Academic Press, New York) using tert-butyloxycarbonyl amino acids and phenylacetamidomethyl resins (Mitchell, A. R. et al., J. Org. Chem. 43:2845 2852 (1978)) or 9-fluorenylmethyloxy-carbonyl amino acids on a polyamide support (Dryland, A. and Sheppard, R. C., J. Chem. So. Perkin Trans. I, 125 137 (1986)). Alternatively, synthetic peptides can be prepared by pepscan synthesis (Geysen, H. M. et al., J. Immunol. Methods 03:259 (1987); Proc. Natl. Acad. Sci. USA 81:3998 (1984)), Cambridge Research Biochemicals, Cambridge, U.K. or by standard liquid phase peptide synthesis.

Peptide substrates may also include a protective group on the amino-end of the peptide. Suitable examples include Carbobenzyloxy (Cbz) group, tert-Butyloxycarbonyl (BOC) group, 9-Fluorenyl-methyloxycarbonyl (FMOC) group, Benzyl(Bn) group, p-methoxyphenyl (PMP) group, Benzyloxy-carbonyl (Z) group, and glutaryl. The use of amino-protecting groups in peptide synthesis is known and is described in, for example, Protective Groups in Organic Chemistry, McOmie, ed., Plenum Press, NY (1973); and Protective Groups in Organic Synthesis, Green ed., John Wiley & Sons, NY (1981), incorporated herein by reference in their entirety.

In a preferred embodiment, peptide substrates are provided that include a cleavage site specifically recognized by the prostate specific antigen (PSA). The term "prostate specific antigen" as used herein includes PSA itself, pharmaceutical acceptable salts of PSA, and other proteases that have the same or substantially the same proteolytic cleavage activity and specificity as PSA. It is known that the PSA cleavage site is located at the carboxyl end of a glutamine or a hydrophobic amino acid like tyrosine, phenylalanine, leucine and isoleucine. Accordingly, a glutamine or a hydrophobic amino acid, and more preferably glutamine, is located at the carboxyl end of the peptide substrate.

The length of the peptide substrate and its water solubility are also an important consideration when constructing the peptide for use in the methods and compositions claimed herein, as they are known to play a role in the ability of PSA and other enzymes to cleave the peptide. Accordingly, the peptide substrates are designed to increase their hydrophilic properties and include at least 3 amino acids. One skilled in the art is undoubtedly capable of constructing a highly water soluble peptide substrate. Generally, a peptide substrates' water solubility can be improved by selecting hydrophilic amino acids or attaching hydrophilic compounds to the peptide.

Examples of suitable peptide substrates for treatment of prostate cancer include, but are not limited to, Hyp-Ala-Ser-Chg-Gln (SEQ ID NO. 1), His-Ser-Ser-Lys-Leu-Gln (SEQ ID NO. 2), and Ser-Ser-Phe-Tyr (SEQ ID NO. 3). Other suitable peptide substrates are disclosed in the following publications: Brady, S. F.; Pawluczyk, J. M.; Lumma, P. K.; Feng, D. M.; Wai, J. M.; Jones, R.; DeFeo-Jones, D.; Wong, B. K.; Miller-Stein, C.; Lin, J. H.; Oliff, A.; Freidinger, R. M.; Garsky, V. M. Design and synthesis of a pro-drug of vinblastine targeted at treatment of prostate cancer with enhanced efficacy and reduced systemic toxicity. J. Med. Chem. 2002, 45, 4706-4715. DeFeo-Jones, D.; Brady, S. F.; Feng, D. M.; Wong, B. K.; Bolyar, T.; Haskell, K.; Kiefer, D. M.; Leander, K.; McAvoy, E.; Lumma, P.; Pawluczyk, J. M.; Wai, J.; Motzel, S. L.; Keenan, K.; Van Zwieten, M.; Lin, J. H.; Garsky, V. M.; Freidinger, R.; Oliff, A.; Jones, R. E. A prostate-specific antigen (PSA)activated vinblastine prodrug selectively kills PSA-secreting cells in vivo. Mol. Cancer Ther. 2002, 1, 451-459. Denmeade, S. R.; Lou, W.; Lovgren, J.; Malm, J.; Lilja, H.; Isaacs, J. T. Specific and efficient peptide substrates for assaying the proteolytic activity of prostate-specific antigen. Cancer Res. 1997, 57, 4924-4930. Akiyama, K.; Nakamura, T.; Iwanaga, S.; Hara, M. The chymotrypsin-like activity of human prostatespecific antigen, y-seminoprotein. FEES Lett. 1987, 225, 168-172. U.S. Patent Appl. Publ. No. 2007-160536, US 6,545,131, PCT Int. Appl. WO 02/043773, PCT Int. Appl. WO 01/093861, U.S. Pat. Appl. Publ. 2003-215456, U.S. Pat. Appl. Publ. 2002-173451, US 5,998,362, PCT Int. Appl. WO 99/28345, PCT Int. Appl. WO 98/10651. The disclosures of the foregoing patent and journal publications are incorporated by reference herein in their entireties. Suitable peptides also include any analog, homolog, mutant, isomer, conservative variations, or derivative of the exemplified peptides, as long as they remain capable of providing substrate for proteolytic cleavage by enzymes specific to tumors responsive to treatment by the chemotherapeutic agent.

Chemotherapeutic Agents:

The term "chemotherapeutic agent" refers to a cytotoxic drug or combination of such drugs commonly used to treat cancer. Typically, the chemotherapeutic agents work by impairing mitosis, effectively targeting fast-dividing cells. As these drugs cause damage to cells they are termed cytotoxic. Linking chemotherapeutic agents to peptide substrates inhibits their cytotoxicity. The cytotoxicity of the chemotherapeutic agent increases when the linker is hydrolyzed thus releasing the chemotherapeutic agent. Conjugate linkers according to the present invention are capable of undergoing 1,6-elimination in vivo upon cleavage of the peptide substrate, so that the cytotoxicity of the cytotoxic agent is essentially fully restored by cleavage of the peptide substrate and hydrolysis of the conjugate linker.

The chemotherapeutic agent is preferably a phosphoramide linked to the peptide substrate through linkers described below attached to the phosphoramide group. Chemotherapeutic agents suitable for use with the present invention contain a phosphoramide group to which the linker can be covalently bonded with a reduction in cytotoxicity.

While the present invention provides methods by which phosphoramides can be conjugated to peptide substrates, the method of the present invention can also be used to covalently attach other classes of chemotherapeutic agents to a linker for the purpose of conjugation to a peptide substrate. Other chemotherapeutic agents covalently attached to a linker via a carbamate or ester include but are not limited to doxobrubicin, taxol, vinblastine, thapsigargen, and their analogs with amino, hydroxyl, phosphate, and carboxylic acid groups. Such groups may be found in the chemotherapeutic agents as commonly provided, or they may be added by chemical synthesis techniques well known in the art without altering the cytotoxicity of the non-conjugated cytotoxic agent. The site of attachment is such that the toxicity of the chemotherapeutic drug is inhibited upon conjugation to the peptide substrate.

Linker:

The linker efficiently releases phosphoramides and other chemotherapeutic agents from the peptide substrate without cytotoxicity inhibiting linker fragments remaining attached to the chemotherapeutic agent. Generally, the linker comprises an aryl moiety having an azide-group at one terminus, a linking group for covalent attachment to the chemotherapeutic agent at another terminus, and, optionally, incorporates one or more ring-substituents such as fluorine on the aryl.

The terms "aryl" and "heteroaryl" refer to any functional group, moiety or substituent derived from a simple aromatic phenyl or pyridine ring, respectively. The azide-group is directly attached to the aryl or heteroaryl, and a chemotherapeutic agent is attached to the arylmethyl or heteroarylmethyl through a phosphate ester, carboxylate ester or carbamate, depending upon the groups available for covalent attachment on the chemotherapeutic agent through which inhibition of the cytotoxic activity of the chemotherapeutic agent by the covalent attachment of the peptide substrate occurs. The azide-group of the linker reacts with the selenocarboxylate of a peptide or amino acid to form an amide bond that can be hydrolyzed by the tumor-specific enzyme.

The linker is hydrolyzed by the tumor-specific enzyme to release the chemotherapeutic agent with essentially the same cytotoxic activity that it possessed prior to conjugation to the peptide substrate through the linker.

In a preferred embodiment, the linker comprises an aminoaryl or aminoheteroaryl moiety, such as for example, an amino-arylmethyl phosphate ester. The linker may have the following chemical formula (7):

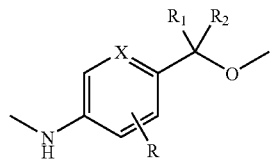

(7)

in which in which $R_1$ and $R_2$ may each independently be a hydrogen, lower alkyl, alkoxyalkyl, carboxylalkyl, or amidoalkyl group; the peptide is a peptide substrate subject to cleavage by a tumor-specific enzyme; X is CH or N; $R_n$ represents up to four electron withdrawing groups and is preferably selected from 2-F, 3-F, 2,6-di-F or 2,3,5,6-tetra-F when X is CH and 3-F, 4-F, 6-F, 3,6-di-F or 3,4,6-tri-F when X is N; wherein the linking of the peptide substrate to the chemotherapeutic agent inhibits the cytotoxic activity of the chemotherapeutic agent, the peptide substrate is subject to proteolytic cleavage by an enzyme specific to a tumor responsive to treatment by the chemotherapeutic agent; and the linker is susceptible to 1,6-elimination in vivo.

The alkyl and lower alkyl groups of $R_1$ and $R_2$ contain up to six carbon atoms. The O atom of the linker forms an ester, carbamate or phosphoramidate when the when couples to a respective carboxylic acid, amide or phosphoramide of a chemotherapeutic agent.

Incorporating the R group decreases electron density of the aryl which increases the stability of the conjugate without affecting cleavage by the tumor-specific enzyme. Accordingly, R may comprise electron-withdrawing functionalities besides the ones presented above. Undoubtedly, a person skilled in the art will be able to make conservative modifications to the linker without undue experimentation to make it more suitable for the purposes of synthesizing a particular conjugate.

In one specific embodiment, the linker includes fluorine substitutions. Fluorine substituents may be located at positions 2, 3, 5, and 6 when X=CH (i.e., 4-amino-benzyl liners) and at positions 3, 4, and 6 when X=N (i.e., 5-aminopyridinyl-2-methyl linkers). Preferably, the fluorine is located at position 2 or position 3 in the case of benzyl linkers and at position 3, 4, or 6 in the case of pyridinyl linkers. Additionally, multiple fluorine substituents may be present on the linker. In one embodiment, the fluorine substituents may be located at position 2 and 6 of the benzyl linker. Alternatively, fluorine substituents may be located at positions 2, 3, 5, and 6 of the benzyl linker. Undoubtedly, a person skilled in the art will realize that other variations in the number and location of fluorine substituents are possible.

Additionally, the stability of the conjugate may be increased by decreasing the electron-donating ability of the nitrogen atom. This may be achieved by, for example, incorporating nitrogen-containing heterocycles on the aryl. The term "heterocycle" refers to a stable 4-8 membered (but preferably, 5 or 6 membered) monocyclic or 8-11 membered bicyclic heterocycle radical which may be either saturated or unsaturated. Each heterocycle consists of carbon atoms and from 1 to 4 heteroatoms chosen from nitrogen, oxygen and sulfur. The heterocycle may be attached by any atom of the cycle, which results in the creation of a stable structure. Unless otherwise specified, the term "heterocycle", when associated with another moiety, shall have the same meaning as given above.

Accordingly, the linker may have the formula (8).

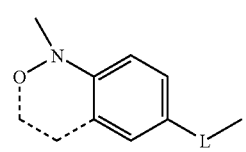

(8)

in which the second ring may be an aromatic or non-aromatic, and may have 3, 4, 5 or 6 members.

Synthesis of Amides from Azides and Carboxylic Acids:

Applicants have developed a new 3-step amidation method that can be carried out under mild conditions and is applicable to amino acids and peptides. Generally, the method reacts an activated terminal carboxylic acid group of an amino acid or peptide with a selenating reagent to form a selenocarboxylate which is then reacted with an azide to form an amide.

The carboxylic acid activating agent may be selected from, but not limited to, chloroformates, 2-(1H-benzotriazol-1-yl)-1,3,3-tetramethyluronium hexafluorophosphate (HBTU), 1-hydroxybenzotriazole hydrate (HOBT), dicyclohexylcarbodiimide (DCC), N-ethyl-N-(3-dimethylaminopropyl)-carbodiimide (EDC), diphenylphosphorylazide (DPPA), benzotriazol-1-yloxytris(di-methylamino) phosphonium hexafluorophosphate (BOP), 1,3-diiso-propylcarbodiimide (DIC) and the like, used in combination or singularly. A carboxylic acid activating agent may be employed in the presence of a base and optionally in the presence of an additive.

The carboxylic acid activating reaction may comprise an additive such as, for example, N-methylpiperidine, diisopropylethylamine, triethylamine, N-methylmorpholine, and lutidine. Solvents suitable for use in these methods include, but are not limited to, THF, N,N-di-methylformamide (DMF), N,N-dimethyl-acetamide (DMAc), N-methyl-pyrrolidinone (NMP), and the like.

By way of non-limiting example, a specific embodiment of the new amidation method is presented in FIG. 1. In step 1, the carboxylic acid group of a Gln-terminal amino acid is activated with an isopropyl chloroformate in THF at 0° C. in the presence of N-methylpiperidine to form the corresponding mixed anhydride. Although isopropyl chloroformate is a preferred activating agent, other chloroformates such as, for example, methyl chloroformate, ethyl chloroformate, and isobutyl chloroformate, may be used. N-methylpiperidine can also be substituted with other bases such as diisopropylethylamine, triethylamine, N-methylmorpholine, and lutidine.

In step 2, the mixed anhydride from step 1 is added to the suspension of a selenating reagent in THF to form a selenocarboxylate. Suitable selenating reagents include, but are not limited to, LiAlHSeH and NaHSe. Preferably, LiAlHSeH or NaHSe is employed to react with the activated carboxylic acid to form a corresponding selenocarboxylate. LiAlHSeH may be prepared by any known method. For example, one method treats LiAlH$_4$ with a stoichiometric amount of selenium in THF at 0° C. to give LiAlHSeH. It is desirable to carry out Step 2 under a nitrogen atmosphere.

In step 3, a solution of an azide-substituted chemotherapeutic agent in an organic solvent is added to the selenocarboxylate solution formed in step 2 to form an amide of the GLN-terminal amino acid. Electron-deficient azides were found to be more reactive, but electron-rich azides may also be used. When electron-rich azides are used, it may be desirable to increase the amount of selenocarboxylate and with mild heating. Suitable electron-deficient azides are presented in, but are not limited to, entries 1 through 6 in FIG. 3, whereas the electron-rich azides include, but are not limited to, the azides listed in entries 7-12 in FIG. 3.

Both protic and aprotic solvents may be used as co-solvents with THF in step 3. Polar organic solvents such as, for example, acetone, methanol, acetonitrile, methyl cyanide or similar, may also be mixed with THF. Preferably, the concentration of the polar solvent in THF is less than 75%, and more preferably between about 25% and 50%. Specific examples include, but are not limited to, 75% THF and 25% CH$_3$COCH$_3$ (v/v), 75% THF and 25% MeOH (v/v), 75% THF and 25% CH$_3$CN (v/v), 50% THF and 50% CH$_3$CN (v/v), and 25% THF and 75% CH$_3$CN (v/v). Additionally, water may also be mixed with THF, preferably in concentration of up to about 25%.

Synthesis of Peptide-Conjugates:

Applicants also developed a new process for synthesizing target-selective chemotherapeutic conjugates of a peptide substrate and a chemotherapeutic agent. Generally, the first step of the method comprises synthesizing an azide compound of formula (4) by a reaction that covalently bonds an azidoaryl compound with a chemotherapeutic agent.

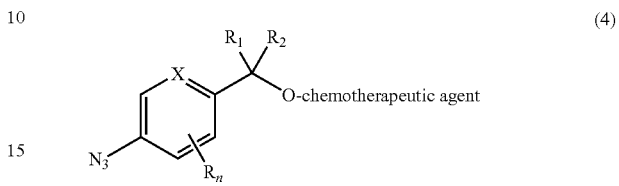

(4)

in which X is CH or N; R is selected from H or an electron-withdrawing group, examples of which include F, Cl, CF$_3$, CN, NO$_2$; n is 0, 1, 2, 3 or 4; R$_1$ and R$_2$ may each independently be a hydrogen, lower alkyl, alkoxyalkyl, carboxylalkyl, or amidoalkyl group; and the chemotherapeutic agent is selected from phosphoramide mustard, taxol, doxorubicin, vinblastine, thapsigargen, and their analogs with amino, hydroxyl, phosphate, and carboxylic acid groups, and the like, covalently bonded to the linker.

The second step of the process reacts an N-protected Gln-selenocarboxylate with the azide from step 1. The preparation of the N-protected Gln-selenocarboxylate of Formula 5, and formation of an amide bond between the carboxyl terminus of Gln and the azide, resulting in the compound of formula 6, is carried out according to amidation methods described above. The reaction results in formation of an N-protected-Gln-amidoaryl.

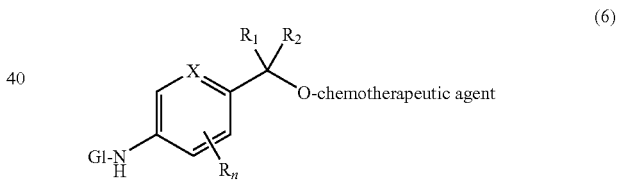

(6)

in which X is CH or N; R is selected from H or an electron-withdrawing group, examples of which include F, Cl, CF$_3$, CN, NO$_2$; n is 0, 1, 2, 3 or 4; R$_1$ and R$_2$ may each independently be a hydrogen, lower alkyl, alkoxyalkyl, carboxylalkyl, or amidoalkyl group; and the chemotherapeutic agent is selected from phosphoramide mustard, taxol, doxorubicin, vinblastine, thapsigargen, and their analogs with amino, hydroxyl, phosphate, and carboxylic acid groups, and the like, covalently bonded to the linker.

Suitable examples of amino protecting groups include, but are not limited to, Carbobenzyloxy (Cbz) group, tert-Butyloxy-carbonyl (BOC) group, 9-Fluorenylmethyloxycarbonyl (FMOC) group, trifluoroacetyl, Benzyl(Bn) group, p-methoxyphenyl (PMP) group, Benzyloxycarbonyl (Z) group, formyl, acetyl, dichloroacetyl, propionyl, hexanoyl, 3,3-diethylhexanoyl. Removal of protecting groups may be accomplished using, for example, ammonia, potassium carbonate, DEA, piperidine, by hydrogenolysis, or by acid treatment. The use of amino-protecting groups is well known to one skilled in the art as described above.

In Step 3, the Gln-amidoaryl group covalently bonded to the chemotherapeutic agent reacts with a protected peptide to form the conjugate of a peptide substrate and the chemotherapeutic agent. The resulting peptide substrate is subject to proteolytic cleavage by enzymes specific to tumors responsive to treatment by the chemotherapeutic agent attached to the peptide. The final step of the process comprises removing the protective group from the peptide, resulting in compound of formula (2):

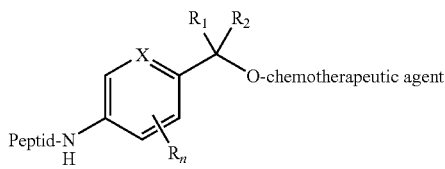

(2)

X is CH or N; R is selected from H or an electron-withdrawing group, examples of which include F, Cl, CF$_3$, CN, NO$_2$, and the like; n is 0, 1, 2, 3 or 4; R$_1$ and R$_2$ may each independently be a hydrogen, lower alkyl, alkoxyalkyl, carboxylalkyl, or amidoalkyl group; and the peptide is a peptide substrate subject to cleavage by a tumor-specific enzyme. R$_n$ may be selected from 2-F, 3-F, 2,6-di-F or 2,3,5,6-tetra-F when X is CH and 3-F, 4-F, 6-F, 3,6-di-F or 3,4,6-tri-F when X is N.

As described above, various chemotherapeutic agents are suitable for synthesizing peptide conjugates according to the Applicant's new process. In preferred embodiments, the chemotherapeutic agents comprise a phosphoramide compound covalently bonded to the linker by the phosphoramidate group. Suitable chemotherapeutic agents include, but are not limited to, phosphoramide mustard, taxol, doxorubicin, vinblastine, thapsigargen, and their analogs with amino, hydroxyl, and carboxylic acid groups, and the like. The TFA-GLN-Se$^-$ can be replaced by a peptide seleno-carboxylate, e.g., Fm-HYP-ALA-SER-CHG-GLN-Se$^-$, in the amidation reaction to form the peptide-Linker-Drug conjugates directly under similar reaction conditions.

Figure 2:
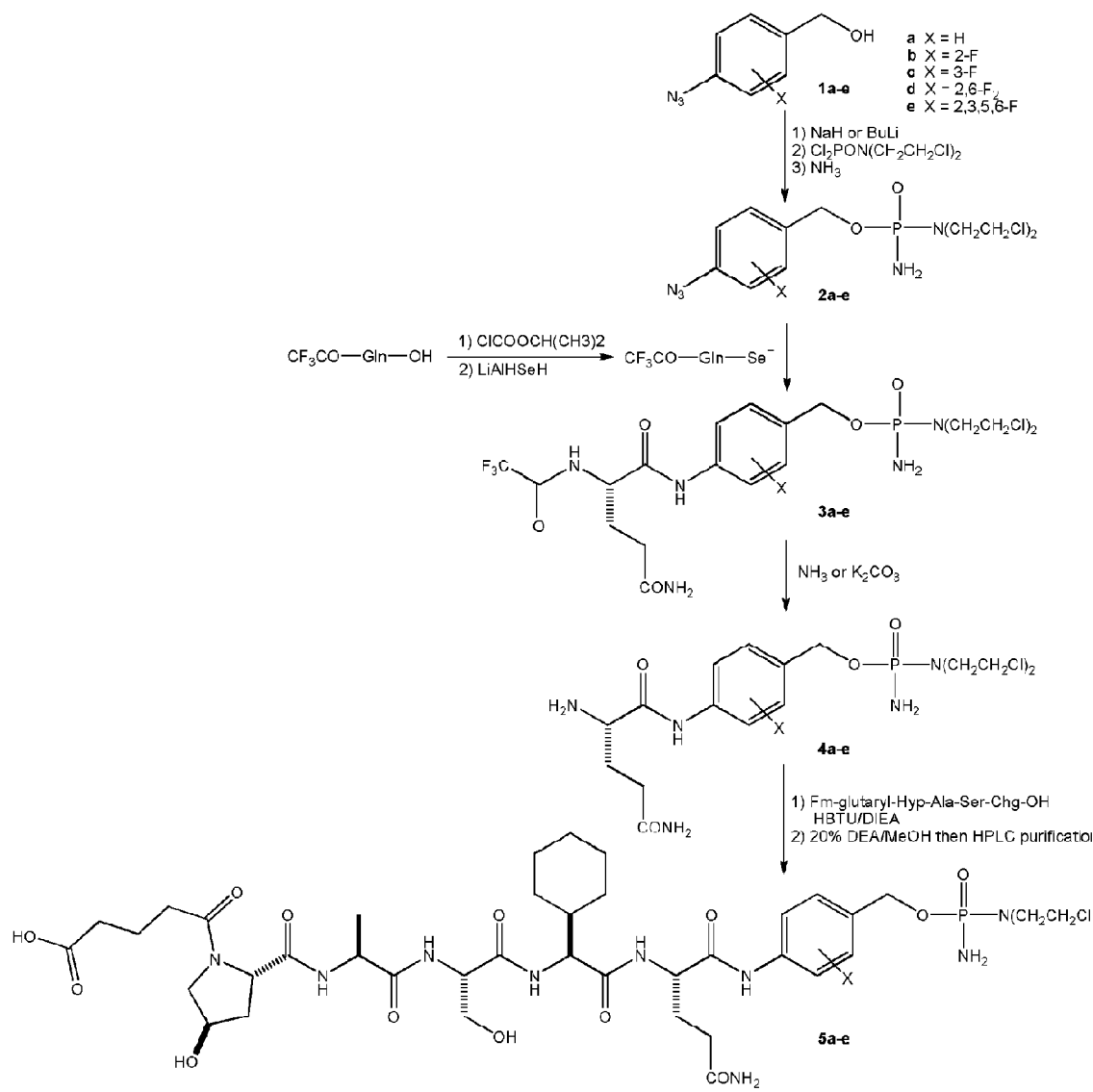
FIG. 2 presents a scheme of the synthesis of a particular chemotherapeutic conjugate.

In one embodiment, peptide-conjugates that can be cleaved by PSA were constructed by attaching a phosphoramide mustard through a linker to a peptide substrate according to the scheme presented in FIG. 2. First, phosphoramide mustard is linked to an azidoaryl in a three-step process, resulting in compound of formula (9).

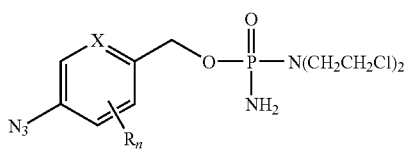

(9)

in which R is selected from H, F, Cl, CF$_3$, CN, NO$_2$, and n is 0, 1, 2, 3 or 4.

More specifically, 4-azidobenzyl alcohols, are deprotonated using NaH or butyl lithium, and the resulting anions are phosphorylated with bis((2-chloroethyl)phosphoramide mustards (H$_2$NPON(CH$_2$CH$_2$Cl)$_2$), followed by bubbling with ammonia to give 4-azidobenzyl phosphoramide mustards (e.g., 2a-e).

Second, a compound comprising a N-protected glutamine amidoaryl group covalently bonded to a phosphoromide mustard is formed. Selenocarboxylates are prepared by activation of N$^\alpha$-Trifluoroacetyl-glutamine with isopropyl chloroformate and treatment with lithium aluminum seleno hydride (LiAlH-SeH) in THF. The selenocarboxylates then react at room temperature with the 4-azidobenzyl phosphoramide mustard to form desired amides (e.g., 3a-e). Removal of trifluoroacetyl protective group using ammonia or potassium carbonate results in compound of formula (10, e.g., 4a-e).

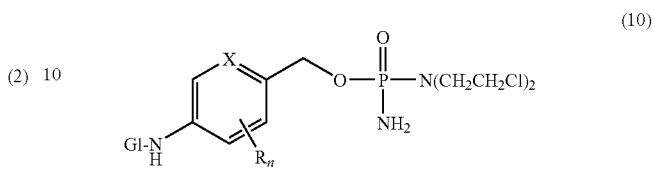

(10)

in which R is selected from H, F, Cl, CF$_3$, CN, NO$_2$, and n is 0, 1, 2, 3 or 4.

After the removal of the trifluoroacetyl protective group using ammonia or potassium carbonate, the amide created in previous step is coupled using HBTU and DIEA to a protected peptide: Fm-glutaryl-Hyp-Ala-Ser-Chg-OH. Finally, deprotection of the peptide is accomplished using diethyl amine (DEA). The resulting compound (e.g., 5a-e) is presented in formula (11):

(11)

in which R is selected from H, F, Cl, CF$_3$, CN, NO$_2$, and n is 0, 1, 2, 3 or 4.

Method of Treatment:

Methods for treating cancer in a patient are also provided. These methods administer to the patient an effective amount of pharmaceutical compositions containing the chemotherapeutic conjugates described above. The peptide is selected to provide a substrate for proteolytic cleavage by an enzyme specific to the type of cancer suffering by the patient and the chemotherapeutic drug is effective in treating that type of cancer. For example, for a patient suffering from a prostate cancer, the chemotherapeutic conjugate couples a substrate susceptible to cleavage by prostate specific antigen with a chemotherapeutic agent typically used for treating prostate cancer.

The terms "treating" and "treatment" of a state, disorder, disease or condition as used herein refers to (1) preventing or delaying the appearance of clinical symptoms of the state, disorder, disease or condition developing in a patient that may be afflicted with or predisposed to the state, disorder, disease or condition but does not yet experience or display clinical or subclinical symptoms of the state, disorder or condition, (2) inhibiting the state, disorder, disease or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a patient to be treated is either statistically significant or at least perceptible to the patient and/or to the physician.

The terms "effective amount" and "therapeutically effective amount" as used herein refer to the amount of a compound that, when administered to a patient for treating a state, disorder, disease or condition, is sufficient to effect such treatment. The effective amount or therapeutically effective amount will vary depending on the compound, the disease and its severity, and the age, weight, physical condition and responsiveness of the individual to be treated.

The terms "delivering" and "administering" as used herein refer to providing a therapeutically effective amount of an active agent to a particular location or locations within a patient causing a therapeutically effective concentration of the active ingredient at the particular location or locations. This can be accomplished, e.g., by local or by systemic administration of the active ingredient to the host.

The term "composition" or "pharmaceutical composition" as used herein refer to a product comprising the specified agent or agents, as well as any product which results, directly or indirectly, from combination of the specified ingredients. The terms are intended to include the combination of an active agent or agents with a carrier, inert or active, making the composition suitable for diagnostic or therapeutic use in vivo, in vitro or ex vivo. The compositions and pharmaceutical composition can also include stabilizers, preservatives, adjuvants, fillers, flavors and other excipients.

Pharmaceutical compositions may be administered in a manner appropriate to the type of cancer being treated (or prevented) as determined by persons skilled in the art. In one embodiment, the composition may be administered parenterally. Examples of parenteral administration are subcutaneous, intravenous, intramascular, intradermal, intrathecal, intraocular, transdermal and general infusion techniques.

Methods for preparation of pharmaceutical compositions are well known in the art. see, e.g., *Remington's Pharmaceutical Sciences* 16th Edition, Easton: Mac Publishing Company (1980). Pharmaceutical compositions comprising peptide substrates may be prepared by methods including, e.g., conventional mixing, dissolving, emulsifying, encapsulating, entrapping, lyophilizing, and spray drying. Pharmaceutical compositions may be formulated in a conventional manner using one or more physiologically acceptable carriers including, e.g., excipients and auxiliaries that facilitate processing of the active agents into preparations that can be used pharmaceutically.

Proper formulation is dependent upon the route of administration chosen. For example, formulations for parenteral administration may be presented in unit dosage form including, for example, ampoules and multi-dose containers, optionally with an added preservative. The compositions may take such forms as suspensions, solutions or emulsions in oily or aqueous vehicles, and may contain formulating materials such as suspending, stabilizing, and/or dispersing agents.

For injection, agents are preferably formulated in aqueous solution, preferably in physiologically compatible buffers or physiological saline buffer. Suitable buffering agents include, e.g, trisodium orthophosphate, sodium bicarbonate, sodium citrate, N-methylglucamine, L(+)-lysine and L(+)-arginine. Solutions of the active agents can be optionally mixed with a nontoxic surfactant. Dispersions can also be prepared in glycerol, liquid polyethylene glycols, triacetin, and mixtures thereof, and in oils. Under ordinary conditions of storage and use, these preparations may contain a preservative to prevent the growth of microorganisms.

Pharmaceutical dosage forms suitable for injection or infusion include, for example, sterile aqueous solutions or dispersions, or sterile powders including the active agent or agents that are adapted for the extemporaneous preparation of sterile injectable or infusible solutions or dispersions, optionally encapsulated in liposomes. In all cases, the ultimate dosage form is preferably sterile, fluid, and stable under the conditions of manufacture and storage. The proper fluidity can be maintained, for example, by the formation of liposomes, by the maintenance of the required particle size in the case of dispersions, or by the use of surfactants. In many cases, it will be preferable to include isotonic agents including, for example, sugars, buffers, or sodium chloride. Prolonged absorption of the injectable compositions can be brought about by the use of agents to delay absorption (e.g., aluminum monostearate, gelatin) in the compositions.

Sterile injectable solutions can be prepared by incorporating the active agent or agents in the required amount in the appropriate solvent with optional ingredients as required (e.g., as enumerated above), followed by, for example, filter sterilization. In the case of sterile powders for the preparation of sterile injectable solutions, preferred methods of preparation include, for example, vacuum drying and freeze drying techniques, which yield a powder of the active ingredient plus any additional desired ingredient present in the previously sterile-filtered solutions.

Other parenteral administrations also include aqueous solutions of a water-soluble form, such as, without limitation, a salt of the active agent or agents. Additionally, suspensions of active agents may be prepared in a lipophilic vehicle. Suitable lipophilic vehicles include, for example fatty oils such as sesame oil, synthetic fatty acid esters such as ethyl oleate and triglycerides, and materials such as liposomes. Aqueous injection suspensions preferably contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

EXAMPLES

Solid-Phase Synthesis of Peptides

All of the peptides, including Fm-glutaryl-Hyp-Ala-Ser-Chg-OH, suc-Ser-Ser-Leu-OH and suc-His-Ser-Ser-Lys-Leu-OH, were synthesized using Fmoc chemistry on 2-methoxy-4-alkoxybenzyl alcohol (SASRIN, 200-400 mesh) resin purchased from Bachem, or 4-hydroxy-methylphenoxy (WANG-type HMP) resin purchased from Advanced Chemtech. $N^\alpha$-Fmoc protected L-amino acids and coupling reagents were purchased from Advanced Chemtech. Side-chain protection was Ser(t-Bu) and Lys(Cl-Z). First amino acid was attached using DMAP/DIC protocol for SASRIN resin and HOBt/DMAP/DIC protocol for WANG resin. All $N^\alpha$-Fmoc protected L-amino acids were used in 3-fold excess for each coupling in NMP. Following completion of the assembly on the resin support, the Fmoc protecting group was removed via the standard 20% piperidine/NMP protocol followed by washing with NMP 5 times and introduction of N-terminal capping group. Deprotection and cleavage of peptides from the resin support were effected using 90% TFA/$CH_2Cl_2$. The benzyl ester and fluorenylmethyl ester (OFm) were not removed under these conditions. After removal of solvents under reduced pressure, the peptides were purified by preparative-HPLC on reverse-phase C18 column. A linear gradient was used from 10% solvent A to 90% solvent B with a flow rate of 12 mL/min, where solvent A was 0.1% TFA/$H_2O$ and solvent B was 0.1% TFA/$CH_3CN$. The UV detection wave-length was set at 220 nm. Homogeneous fraction containing the desired products were pooled and lyophilized to afford the peptides as a white powder. The purity and identity were confirmed by LC/MS.

Synthesis of 4-azido-arylmethylphosphoramide Mustards (2a-e)

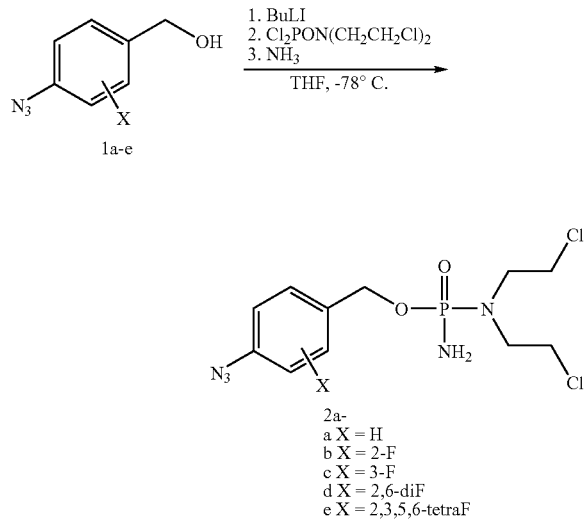

To a solution of the alcohol 1a-e (5.0 mmol) in anhydrous THF (25 mL) was added a solution of BuLi in cyclohexane (2.0 M, 2.75 mL) at −78° C. After 20 min, the above solution was trans-ferred to a pre-cooled solution of bis(2-chloroethyl) phosphor-amidic di-chloride (1.43 g, 5.5 mmol) in THF (25 mL) at −78° C. via a cannula. The resulting mixture was stirred at −78° C. for 5 h followed by bubbling with ammonia for 10 min. The reaction mixture was allowed to gradually warm up to room temperature over 2 h. After removal of THF via distillation under reduced pressure, the residue was suspended in saturated aqueous sodium bicarbonate (50 mL) followed by extraction with dichloromethane (3×50 mL). The combined organic phase was washed with water (50 mL) and saturated brine (50 mL), and dried over $Na_2SO_4$. After filtration to remove $Na_2SO_4$, the filtrate was concentrated to dryness under reduced pressure. The crude product was purified by flash column chroma-tography (di-chloromethane to 5% methanol in dichloromethane) to afford the following desired products.

4-azido-benzylphosphoramide mustard (2a): a yellow semi-solid (0.965 g, 55%); $^1$H NMR (200 MHz, $CD_3OD$): δ 7.45 (d, 2H, J=8.4 Hz), 7.09 (d, 2H, J=8.4 Hz), 4.97 (d, 2H, J=7.4 Hz), 3.61-3.69 (m, 4H), 3.33-3.48 (m, 4H); $^{13}$C NMR (50 MHz, $CD_3OD$): 139.5, 133.3 (d, J=8.0 Hz), 128.6, 118.2, 65.7 (d, J=5.0 Hz), 48.8 (d, J=5.0 Hz), 41.2; IR (film): 3415, 3003, 1655, 1437, 1407, 1315, 1022, 953 $cm^{-1}$; MS ($ESI^+$): m/z (intensity), 352.1 ($[M+H]^+$, 100%), 354.1 ($[M+H]^+$+2, 65%), 356.1 ($[M+H]^+$+4, 10%), 393.2 ($[M+H]^+$+ acetonitrile, 20%), 395.2 ($[M+H]^+$+2+ acetonitrile, 13%, 397.2 $[M+H]^+$ 4+ acetonitrile, 2%).

4-azido-2-fluorobenzylphosphoramide mustard (2b): a yellow semi-solid (0.959 g, 52%); $^1$H NMR (200 MHz, $CDCl_3$): δ 7.24 (t, 1H, J=8.0 Hz), 6.63 (dd, 1H, J=2.2 Hz, J=8.0 Hz), 6.53 (dd, 1H, J=2.2 Hz, J=8.0 Hz), 4.79 (d, 2H, J=7.2 Hz), 3.49 (d, —$NH_2$, J=5.4 Hz), 3.28-3.45 (m, 4H), 3.13-3.26 (m, 4H); $^{13}$C NMR (50 MHz, $CDCl_3$): 161.2 (d, J=248.9 Hz), 142.2 (d, J=9.9 Hz), 131.5 (d, J=5.4 Hz), 120.2 (dd, J=15.0 Hz, J=8.0 Hz), 114.8 (d, J=3.4 Hz), 106.6 (d, J=25.0 Hz), 60.7 (d, J=8.0 Hz), 49.1 (d, J=5.0 Hz), 42.4; IR (film): 3431, 2118, 1621, 1505, 1303, 1214, 1091, 1012, 980 $cm^{-1}$; MS ($ESI^+$): m/z (intensity), 370.1 ($[M+H]^+$, 100%), 372.1 ($[M+H]^+$+2, 65%), 374.1 ($[M+H]^+$+4, 10%), 411.1 ($[M+H]^+$ acetonitrile, 20%), 413.1 ($[M+H]^+$+2+ acetonitrile, 13%, 415.1 ($[M+H]^+$+4+ acetonitrile, 2%).

4-azido-3-fluorobenzylphosphoramide mustard (2c): a yellow semi-solid (0.959 g, 52%); $^1$H NMR (200 MHz, $CDCl_3$): δ 7.06-7.25 (m, 3H), 5.00 (dd, 2H, J=7.8 Hz, J=4.0 Hz), 3.66-3.73 (m, 4H), 3.43-3.55 (m, 4H); $^{13}$C NMR (50 MHz, $CDCl_3$): 154.3 (d, J=248.5 Hz), 134.7 (dd, J=7.5 Hz, J=7.5 Hz), 127.4 (d, J=10.0 Hz), 123.7 (d, J=3.5 Hz), 120.8, 115.7 (d, J=19.7 Hz), 65.5 (d, J=8.0 Hz), 48.9 (d, J=4.6 Hz), 42.3; IR (film): 3424, 2134, 2099, 1643, 1509, 1218, 983 $cm^{-1}$; MS ($ESI^+$): m/z (intensity), 370.10 ($[M+H]^+$, 100%), 372.10 ($[M+H]^+$+2, 65%), 374.10 ($[M+H]^+$+4, 10%), 411.1 ($[M+H]^+$+ acetonitrile, 30%), 413.1 ($[M+H]^+$+2+ acetonitrile, 20%, 415.1 ($[M+H]^+$+4+ acetonitrile, 3%).

4-azido-2,6-difluorobenzylphosphoramide mustard (2d): a light yellow solid (0.970 g, 50%); $^1$H NMR (200 MHz, $CD_3OD$): δ 6.72 (d, 2H, J=8.4 Hz), 4.95 (d, 2H, J=7.0 Hz), 3.52-3.60 (m, 4H), 3.26-3.39 (m, 4H); $^{13}$C NMR (50 MHz, $CD_3OD$): 163.6 (dd, J=250.0 Hz, J=9.5 Hz), 145.2 (t, J=13.3 Hz), 110.5 (dt, J=20 Hz, J=8.4 Hz), 103.9 (dd, J=29.6 Hz, J=2.0 Hz), 55.4 (dd, J=8.0 Hz, J=3.8 Hz), 50.6 (d, J=4.6 Hz), 43.0; MS ($ESI^+$): m/z (intensity), 388.2 ($[M+H]^+$, 100%), 390.2 ($[M+H]^+$+2, 65%), 392.2 ($[M+H]^+$+4, 10%), 429.3 ($[M+H]^+$+ acetonitrile, 20%), 431.3 ($[M+H]^+$+2+ acetonitrile, 13%), 433.3 ($[M+H]^+$+4+ acetonitrile, 2%).

4-azido-2,3,5,6-tetrafluorobenzylphosphoramide mustard (2e): a dark green solid (1.02 g, 48%); $^1$H NMR (200 MHz, $CD_3OD$): δ 5.03 (d, 2H, J=7.8 Hz), 3.55-3.62 (m, 4H), 3.32-3.41 (m, 4H); $^{13}$C NMR (50 MHz, $CD_3OD$): 146.7 (dm, J=251.0 Hz), 141.9 (dm, J=248.0 Hz), 121.0 (tt, J=12.2 Hz J=3.0 Hz), 110.4 (td, J=12.4 Hz J=8.4 Hz), 54.2, 49.1 (d, J=5.0 Hz), 42.3; IR (film): 3443, 3241, 3113, 2964, 2159, 2124, 1654, 1496, 1238, 984 $cm^{-1}$; MS ($ESI^+$): m/z (intensity), 424.0 ($[M+H]^+$, 100%), 426.0 ($[M+H]^+$+2, 65%), 428.0 ($[M+H]^+$+4, 10%), 465.1 ($[M+H]^+$+ acetonitrile, 20%), 467.1 ($[M+H]^+$+2+ acetonitrile, 13%), 469.1 ($[M+H]^+$+4+ acetonitrile, 2%).

Synthesis of 4-($N^α$-Trifluoroacetyl-L-glutaminyl) amido-arylmethyl Phosphoramide Mustards (3a-e)

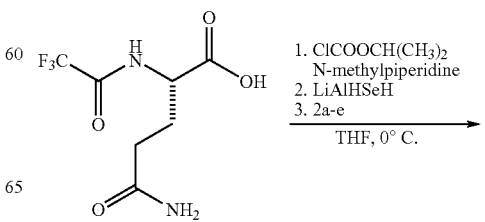

-continued

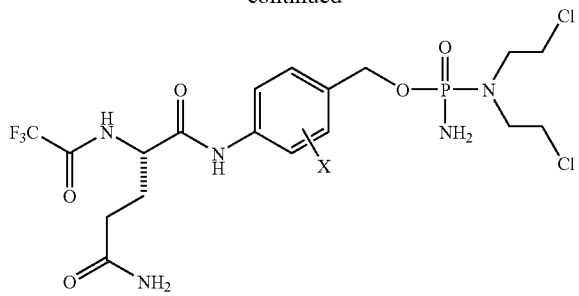

3a-e
a X = H
b X = 2-F
c X = 3-F
d X = 2,6-di-F
e X = 2,3,5,6-tetra-F

To a solution of N-trifluoroacetyl glutamine (2.0 mmol) and N-methylpiperidine (0.244 mL, 2.0 mmol) in THF (10 mL) was added a solution of isopropyl chloroformate in toluene (2.0 mL, 2.0 mmol) at −15° C. The resulting mixture was stirred for 30 minutes at −15 to −10° C. Then, the resulting mixed anhydride solution was added into the freshly prepared solution of LiAlHSeH in THF via cannu-lation over a period of 5 min. The reaction mixture was stirred for an additional 30 min below 5° C. under a nitrogen atmosphere. Then, a solution of azide 2a-e (1.0 mmol) in THF (1 mL) was added into the above selenocarboxylate solution via syringe. The reaction was carried out at room temperature for 24 h. After evaporation of THF, the residue was suspended in a saturated aqueous sodium bicarbonate solution (25 mL) followed by extraction with dichloromethane (4×50 mL). The combined organic phase was washed with 1.0 N HCl (50 mL), water (50 mL) and brine (50 mL), and dried over $Na_2SO_4$. After removal of $Na_2SO_4$ through filtration, the filtrate was concentrated to dryness under reduced pressure. The crude product was purified by flash column chromatography (FCC) (dichloromethane to 10% methanol in dichloromethane) on silica gel to provide following desired products.

4-($N^\alpha$-Trifluoroacetyl-L-glutaminyl)amidobenzylphosphoramide mustard (3a): a yellow semi-solid (137 mg, 25%); $^1$H NMR (200 MHz, $CD_3OD$): δ 7.62 (d, 2H, J=8.4 Hz), 7.39 (d, 2H, J=8.4 Hz), 4.97 (d, 2H, J=7.2 Hz), 4.56 (dd, 1H, J=8.0 Hz, J=5.4 Hz), 3.61-3.68 (m, 4H), 3.32-3.41 (m, 4H), 2.38-2.45 (m, 2H), 2.09-2.27 (m, 2H); $^{13}$C NMR (50 MHz, $CD_3OD$): 175.5, 168.7, 157.2 (q, J=37.5 Hz), 137.5, 132.5 (d, J=7.5 Hz), 127.6, 119.5, 115.3 (q, J=285.0 Hz), 65.9 (d, J=5.5 Hz), 53.5, 48.8 (d, J=5.0 Hz), 41.2, 30.3, 26.4; IR (film): 3261, 3063, 2959, 1715, 1608, 1545, 1213, 1185, 1159, 1011, 980 cm$^{-1}$; MS (ESI$^+$): m/z (intensity), 572.1 ([M+Na]$^+$ 100%), 574.1 ([M+Na]$^+$+2, 65%), 576.1 ([M+Na]$^+$+4, 10%).

4-($N^\alpha$-Trifluoroacetyl-L-glutaminyl)amido-2-fluorobenzyl phosphoramide mustard (3b): a yellow semi-solid (255 mg, 45%); $^1$H NMR (200 MHz, $CD_3OD$): δ 7.84 (dd, 1H, J=1.8 Hz, J=12.4 Hz), 7.66 (t, 1H, J=8.2 Hz), 7.54 (dd, 1H, J=1.8 Hz, J=12.4 Hz), 5.21 (d, 2H, J=6.8 Hz), 4.75 (dd, 1H, J=8.0 Hz, J=5.2 Hz), 3.80-3.89 (m, 4H), 3.58-3.68 (m, 4H), 2.57-2.67 (m, 2H), 2.09-2.27 (m, 2H); IR (film): 3404, 2962, 2760, 1666, 1627, 1549, 1189, 1161, 998 cm$^{-1}$; MS (ESI$^+$): m/z (intensity), 348.2 ([M—OP(O)NH$_2$N(CH$_2$CH$_2$Cl)$_2$]$^+$, 25%), 366.3 ([M—OP(O)NH$_2$N(CH$_2$CH$_2$Cl)$_2$]$^+$+H$_2$O, 100%), 407.3 ([M—OP(O)NH$_2$N(CH$_2$CH$_2$Cl)$_2$]$^+$+H$_2$O+acetonitrile, 40%), 590.3 ([M+Na]$^+$+4, 20%), 592.3 ([M+H]$^+$+2, 13%), 594.3 ([M+Na]$^+$4, 2%).

4-($N^\alpha$-Trifluoroacetyl-L-glutaminyl)amido-3-fluorobenzyl phosphoramide mustard (3c): a yellow semi-solid (113 mg, 20%); $^1$H NMR (200 MHz, $CD_3OD$): δ 7.83 (t, 1H, J=8.0 Hz), 7.15-7.26 (m, 2H), 4.93 (d, 2H, J=7.2 Hz), 4.61 (dd, 1H, J=8.0 Hz, J=5.2 Hz), 3.59-3.66 (m, 4H), 3.33-3.45 (m, 4H), 2.37-2.44 (m, 2H), 2.09-2.27 (m, 2H); IR (film): 3404, 2962, 2760, 1666, 1627, 1549, 1189, 1161, 998 cm$^{-1}$; MS (ESI$^+$): m/z (intensity), 348.2 ([M—OP(O)NH$_2$N(CH$_2$CH$_2$Cl)$_2$]$^+$, 100%), 366.3 ([M—OP(O)NH$_2$N(CH$_2$CH$_2$Cl)$_2$]$^+$+H$_2$O, 55%), 407.3 ([M—OP(O)NH$_2$N(CH$_2$CH$_2$Cl)$_2$]$^+$+H$_2$O+acetonitrile, 15%), 568.3 ([M+H]$^+$, 40%), 570.3 ([M+H]$^+$+2, 26%), 572.3 ([M+H]$^+$+4, 4%), 590.3 ([M+Na]$^+$30%), 592.3 ([M+Na]$^+$+2, 20%), 594.3 ([M+Na]$^+$+4, 3%).

4-($N^\alpha$-Trifluoroacetyl-L-glutaminyl)amido-2,6-difluorobenzyl phosphoramide mustard (3d): a yellow semi-solid (322 mg, 55%); $^1$H NMR (200 MHz, $CD_3OD$): δ 7.31 (d, 1H, J=9.6 Hz), 5.00 (d, 2H, J=7.0 Hz), 4.50 (dd, 1H, J=8.6 Hz, J=5.2 Hz), 3.53-3.64 (m, 4H), 3.33-3.44 (m, 4H), 2.30-2.41 (m, 2H), 2.04-2.25 (m, 2H); $^{13}$C NMR (50 MHz, $CD_3OD$): 177.3, 170.9, 163.0 (dd, J=246.5 Hz, J=10.0 Hz), 159.1 (q, J=37.5 Hz), 142.4 (t, J=14.0 Hz), 117.3 (q, J=285.0 Hz), 109.2 (dt, J=20 Hz, J=8.4 Hz), 103.7 (d, J=30.0 Hz), 55.4, 50.6, 50.4, 42.9, 32.0, 28.0; IR (film): 3295, 3075, 2966, 1698, 1668, 1615, 1556, 1425, 1215, 1012, 935 cm$^{-1}$; MS (ESI$^-$): m/z (intensity), 584.1 ([M−H]$^-$, 100%), 586.1 ([M−H]$^-$+2, 65%), 588.1 ([M−H]$^-$+2, 10%), 698.1 ([M−H]$^-$+TFA, 40%), 700.1 ([M−H]$^-$+TFA, 26%), 702.1 ([M−H]$^-$+TFA, 4%).

4-($N^\alpha$-Trifluoroacetyl-L-glutaminyl)amido-2,3,5,6-tetrafluoro-benzyl phosphoramide mustard (3e): a yellow semi-solid (298 mg, 48%); $^1$H NMR (200 MHz, $CD_3OD$): δ 5.13 (d, 2H, J=7.6 Hz), 4.66 (dd, 1H, J=8.0 Hz, J=5.2 Hz), 3.60-3.68 (m, 4H), 3.37-3.47 (m, 4H), 2.40-2.47 (m, 2H), 2.07-2.27 (m, 2H); $^{13}$C NMR (50 MHz, $CD_3OD$): 177.3, 171.3, 159.2 (q, J=37.5 Hz), 147.6 (dm, J=245.0 Hz), 143.7 (dm, J=245.0 Hz), 118.5 (t, J=14.8 Hz), 117.5 (q, J=285.0 Hz), 115.0 (td, J=17.7 Hz, J=8.0 Hz), 55.5, 54.8, 50.6 (d, J=4.9 Hz), 43.0, 32.0, 28.0; MS (ESI$^-$): m/z (intensity), 620.1 ([M−H]$^-$, 100%), 622.1 ([M−H]$^-$+2, 65%), 624.1 ([M−H]$^-$+4, 10%).

Synthesis of 4-L-glutaminylamido-arylmethyl phosphoramide Mustards (4a-e)

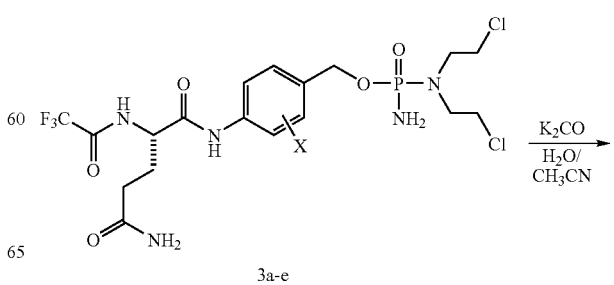

3a-e

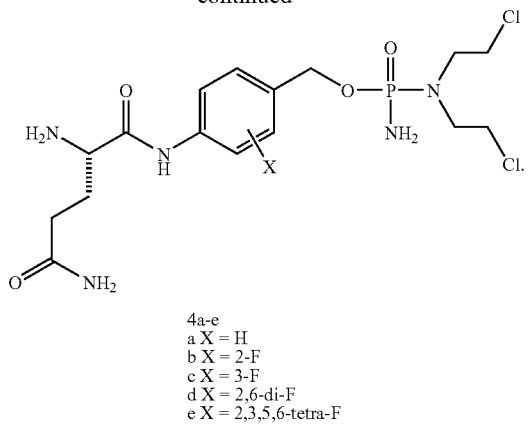

4a-e
a X = H
b X = 2-F
c X = 3-F
d X = 2,6-di-F
e X = 2,3,5,6-tetra-F

A solution of the 4-(N$^\alpha$-Trifluoroacetyl-L-glutaminyl) amido-arylmethyl phosphoramide mustard (3a-e) (1.0 mmol) and potassium carbonate (552 mg, 4.0 mmol) in 75% aqueous acetonitrile (20 mL) was stirred at room temperature for 48 h. The completion of the reaction was confirmed by LC/MS and TLC. The aqueous phase was saturated with sodium chloride followed by extraction with acetonitrile (3×10 mL). The combined acetonitrile phase was dried over Na$_2$SO$_4$ followed by filtration to remove Na$_2$SO$_4$. The filtrate was concentrated to dryness to afford the desired product (4a-e) that was used directly in the next step without further purification.

Synthesis of glutaryl-Hyp-Ala-Ser-Chg-Gln-NH-arylmethyl phosphor-amide Mustards (5a-e)

To a solution of Fm-glutaryl-Hyp-Ala-Ser-Chg-OH (0.1 mmol) and HBTU (0.11 mmol) in NMP (2 mL) was added DIPEA (0.11 mmol). The resulting mixture was stirred at room temperature for 30 min followed by the addition of a solution of 4a-e (0.1 mmol) in NMP (0.5 mL). The reaction was carried out at room temperature for additional 2 h and quenched by adding ice-cold 5% aqueous sodium bicarbonate (10 mL). The resulting mixture was stirred at 0-5° C. for 10 min and the resulting white precipitates were collected via centrifugation followed by successively washing with distilled water. The resulting solid was then dissolved in 50% MeOH/CH$_3$CN and treated with 10 equiv of DEA for 1 h. After removal of solvents under reduced pressure, the remaining solid was suspended in diethyl ether and collected via centrifugation. The crude products were purified by preparative-HPLC on reverse-phase C18 column. A linear gradient was used from 10% solvent A to 90% solvent B with a flow rate of 12 mL/min, where solvent A was 0.1% TFA/H$_2$O and solvent B was 0.1% TFA/CH$_3$CN. The UV detection wavelength was set at 220 nm. Homogeneous fraction containing the desired products were pooled and lyophilized to afford the desired products as white powders. The purity and identity of products were confirmed by LC/MS.

glutaryl-Hyp-Ala-Ser-Chg-Gln-NH-benzyl phosphoramide mustard (5a): white powder (30 mg, 30%); HRMS (FAB+) m/z calc'd for C$_{40}$H$_{62}$C$_{12}$N$_9$NaO$_{13}$P, [M+Na]$^+$, as 1000.3479, found 1000.3477.

glutaryl-Hyp-Ala-Ser-Chg-Gln-NH-2-fluorobenzyl phosphoramide mustard (5b): white powder (40 mg, 38%); HRMS (FAB$^+$) m/z calc'd for C$_{40}$H$_{61}$Cl$_2$FN$_9$NaO$_{13}$P [M+Na]$^+$, 1018.3385, found 1018.3357.

glutaryl-Hyp-Ala-Ser-Chg-Gln-NH-3-fluorobenzyl phosphoramide mustard (5c): white powder (28 mg, 28%); HRMS (FAB$^+$) m/z calc'd for C$_{40}$H$_{61}$Cl$_2$FN$_9$NaO$_{13}$P [M+Na]$^+$, 1018.3385, found 1018.3363.

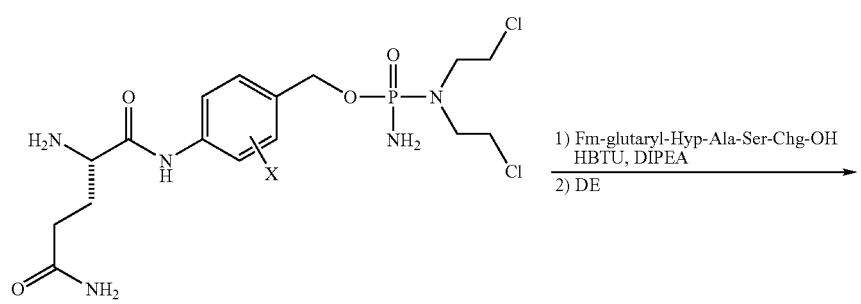

4a-e

1) Fm-glutaryl-Hyp-Ala-Ser-Chg-OH HBTU, DIPEA
2) DE

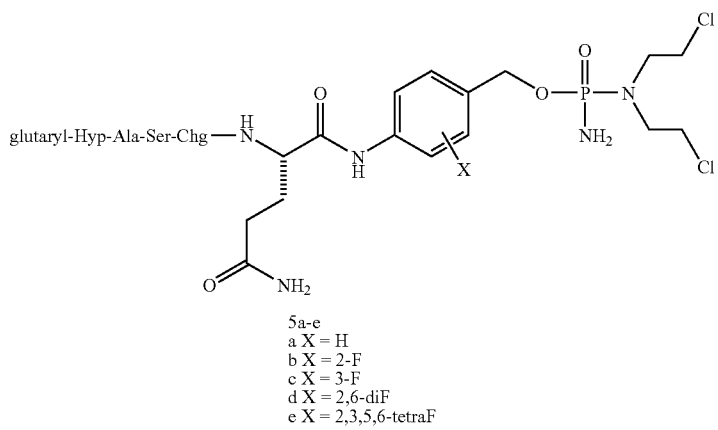

5a-e
a X = H
b X = 2-F
c X = 3-F
d X = 2,6-diF
e X = 2,3,5,6-tetraF glutaryl-Hyp-Ala-Ser-Chg-Gln-NH-2,6-difluorobenzyl phosphoramide mustard (5d): white powder (41 mg, 40%); HRMS (FAB$^+$) m/z calc'd for $C_{40}H_{60}Cl_2F_2N_9NaO_{13}P$ [M+Na]$^+$, 1036.3291, found 1036.3181.

glutaryl-Hyp-Ala-Ser-Chg-Gln-NH-2,3,5,6-tetrafluorobenzyl phosphoramide mustard (5e): white powder (32 mg, 30%); HRMS (FAB$^+$) m/z calc'd for $C_{40}H_{58}Cl_2F_4N_9NaO_{13}P$ [M+Na]$^+$, 1072.3103, found 1072.2985.

When TLC and/or LC-MS showed the disappearance of the starting azide or no further change of the reaction mixture, the reaction mixture was filtered through a Celite pad that was then rinsed with EtOAc (3×25 mL). The combined organic phase was washed with 5% NaHCO$_3$, water, and brine and dried over anhydrous Na$_2$SO$_4$. After removal of Na$_2$SO$_4$ through filtration, the filtrate was treated with activated charcoal. The activated charcoal was filtered off, and the filtrate was then concentrated to dryness. The crude product was purified by flash column chromatography (FCC) on silica gel. Yields and physical and spectroscopic data of all amides are consistent with their structures.

Stability and PSA Cleavage of Glutaryl-Hyp-Ala-Ser-Chg-Gln-amino-benzyl Phosphoramide Mustards First, the stability and PSA cleavage of glutaryl-Hyp-Ala-Ser-Chg-Gln-aminobenzyl phosphoramide mustard without substitutions on the benzyl ring (5a) was tested by monitoring the disappearance of the peptide-linker-drug conjugate using HPLC. It was found that conjugate 5a was slowly decomposed with a half life of 48 h in 0.1 M phosphate buffer, pH 7.4, at 37° C. In the presence of PSA, the peptide-linker-drug conjugate 5a was quickly hydrolyzed with a half life of 1.2 h. Thus, peptide-linker-drug conjugate 5a is a substrate of PSA. The hydrolysis in the presence of PSA was 40 times faster than that in the absence of PSA. But, the instability in the absence of PSA was a concern. This instability can be addressed by introducing an electron-withdrawing fluorine atom on the aromatic ring as shown in Table 1. Both 2-F (5b) and 3-F (5c) substituent are much more stable than 5a in the absence of PSA. In the presence of PSA, they were more quickly hydrolyzed with t½ of 43 and 57 min, respectively.

Selective cytotoxicity of glutaryl-Hyp-Ala-Ser-Chg-Gln-aminobenzyl phosphoramide mustards toward PSA-producing LNCaP cells as compared to non-PSA-producing DU145 cells in an in vitro assay Two prostate cancer cell lines have been used for in vitro antiproliferative activity assay of prodrugs designed for PSA activation: an androgen-sensitive LNCaP human prostate cancer cell line that expresses PSA and an androgen-insensitive DU145 human prostate cancer cell line that does not express PSA. The cell culture results compiled in Table 1 clearly indicate that 5a, the first conjugate synthesized in this series, is selectively more cytotoxic to PSA-producing LNCaP cells with an IC$_{50}$ of 11 μM relative to about 35 μM in DU145 cells after 72 h drug exposure. The cytotoxicity to DU145 cells that do not express PSA could be due to the slow decomposition of conjugate 5a, which has a t½ of 48 h. The corresponding nitrobenzyl phosphoramide mustard (LH7) is stable and much less cytotoxic (Y. Jiang, J. Han, C. Yu, S. O. Vass, P. F. Searle, P. Browne, R. J. Knox, L. Hu J. Med. Chem. 2006, 49(14), 4333-4343) suggesting that proteolysis of peptide amido-benzyl phosphoramide mustard such as 5a was less effective as a trigger when compared to nitroreductase reduction of —NO$_2$→—NHOH. Furthermore, analogs 5b and 5c were synthesized with an electron-withdrawing fluorine atom at C2 (5b) and C3 (5c), respectively. Results indicate that analogs 5b and 5c not only have improved yields of amidation between selenocarboxylate and azide but also are much more stable and selective than 5a as shown in Table 1.

TABLE 1

Stability, PSA cleavage, and antiproliferative activity of the Peptide-Linker-Drug conjugates 5a-e:

| | | $T_{1/2}$ (h)$^a$ | | | IC50 (μM) | | |
|---|---|---|---|---|---|---|---|
| ID | Peptide-Linker-Drug Conjugate | −PSA | +PSA | Ratio$^b$ | LNCaP | DU145 | Selectivity$^c$ |
| 5a | glutaryl-Hyp-Ala-Ser-Chg-Gln-NH-benzyl PM | 48 | 1.1 | 40 | 11 | 35 | 3 |
| 5b | glutaryl-Hyp-Ala-Ser-Chg-Gln-NH-2F-benzyl PM | 105 | 0.93 | 113 | 5.3 | >100 | >19 |
| 5c | glutaryl-Hyp-Ala-Ser-Chg-Gln-NH-3F-benzyl PM | 462 | 0.65 | 711 | 29 | >100 | >3 |
| 5d | glutaryl-Hyp-Ala-Ser-Chg-Gln-NH-2,6-diF-benzyl PM | 131 | 1.75 | 75 | 20 | >100 | >5 |
| 5e | glutaryl-Hyp-Ala-Ser-Chg-Gln-NH-2,3,5,6-tetraF-benzyl PM | 178 | 1.1 | 162 | >100 | >100 | NA |

$^a T_{1/2}$ in the absence of PSA indicates the stability of Peptide-Linker-Drug conjugates while $T_{1/2}$ in the presence of PSA indicates effectiveness of PSA-catalyzed cleavage.
$^b$Stability Ratio is calculated between the $T_{1/2}$ values in the absence and presence of PSA.
$^c$Selectivity is calculated as a ratio of IC$_{50}$ in non-PSA-producing DU145 and IC$_{50}$ in PSA-producing LNCaP.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A target-selective chemotherapeutic conjugate of a peptide substrate to a chemotherapeutic agent, said conjugate comprising a peptide covalently linked to the cytotoxic chemotherapeutic agent by a linker of formula:

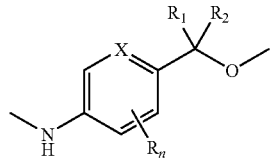

wherein X is N; $R_1$ and $R_2$ are independently selected from the group consisting of hydrogen, lower alkyl, alkoxyalkyl, amidoalkyl and carboxylalkyl; the terminal O on said linker forms a carboxylate, carbamate, phosphate, or phosphoramidate with said chemotherapeutic agent; and R is selected from the group consisting of F and Cl and n is 0, 1, 2, 3, 4;

wherein said chemotherapeutic conjugate is less cytotoxic than said chemotherapeutic agent; said peptide substrate is subject to proteolytic cleavage by a tumor-specific enzyme;

after which said linker undergoes 1,6-elimination in vivo to release said cytotoxic agent.

2. The chemotherapeutic conjugate of claim 1 wherein said peptide substrate comprises at least 3 amino acids, one of which is a Gln attached to the amino-end of said linker.

3. The chemotherapeutic conjugate of claim 1 wherein the peptide substrate is selected from the group consisting of Hyp-Ala-Ser-Chg-Gln (SEQ ID NO: 1), His-Ser-Ser-Lys-Leu-Gln (SEQ ID NO: 2) and Ser-Ser-Phe-Tyr (SEQ ID NO: 3).

4. The chemotherapeutic conjugate of claim 1, wherein said chemotherapeutic agent is selected from the group consisting of phosphoramide mustard, taxol, doxorubicin, vinblastine, thapsigargen and cytotoxic analogs thereof with amino, hydroxyl, carboxylic acid, phosphate, and phosphoramidate groups.

5. A method for treating prostate cancer in a patient comprising administering to said patient a composition comprising the target-selective chemotherapeutic conjugate of claim 1, wherein said peptide of said conjugate is a substrate for proteolytic cleavage of prostate specific antigen (PSA).

* * * * *